(12) United States Patent
Winfree et al.

(10) Patent No.: US 9,186,173 B2
(45) Date of Patent: Nov. 17, 2015

(54) OPTICAL OBTURATOR SYSTEM

(71) Applicants: Alan Winfree, Franklin, TN (US); Stan Ashburn, Clarksville, TN (US)

(72) Inventors: Alan Winfree, Franklin, TN (US); Stan Ashburn, Clarksville, TN (US)

(73) Assignee: Specialty Care, Inc., Nashville, TN (US)

( * ) Notice: Subject to any disclaimer, the term of this patent is extended or adjusted under 35 U.S.C. 154(b) by 460 days.

(21) Appl. No.: 13/872,856

(22) Filed: Apr. 29, 2013

(65) Prior Publication Data

US 2013/0289600 A1    Oct. 31, 2013

Related U.S. Application Data

(60) Provisional application No. 61/639,225, filed on Apr. 27, 2012.

(51) Int. Cl.
*A61B 17/34* (2006.01)
*A61B 19/00* (2006.01)
*A61B 17/00* (2006.01)
*A61B 17/221* (2006.01)

(52) U.S. Cl.
CPC ......... *A61B 17/3417* (2013.01); *A61B 19/5212* (2013.01); *A61B 2017/00907* (2013.01); *A61B 2017/2217* (2013.01); *A61B 2017/346* (2013.01)

(58) Field of Classification Search
CPC ............... A61B 17/3417; A61B 17/34; A61B 17/3401; A61B 17/3415; A61B 17/3421; A61B 17/320016; A61B 17/32053; A61B 17/3209; A61B 17/32093; A61B 17/3478; A61B 17/3468; A61B 2017/3454; A61B 2017/346; A61B 2017/00296; A61B 2017/00292; A61B 2010/045; A61B 1/00096; A61B 1/00101; A61B 1/00087; A61B 1/3417
See application file for complete search history.

(56) References Cited

U.S. PATENT DOCUMENTS

| 5,242,412 A | 9/1993 | Blake, III | |
| 5,246,425 A * | 9/1993 | Hunsberger | A61B 17/3496 604/164.12 |
| 5,256,149 A | 10/1993 | Banik et al. | |
| 5,271,380 A * | 12/1993 | Riek | A61B 1/00165 600/104 |
| 5,330,501 A * | 7/1994 | Tovey | A61B 17/3421 604/105 |

(Continued)

FOREIGN PATENT DOCUMENTS

| DE | 10333956 | 2/2005 |
| EP | 0665029 | 1/1995 |

(Continued)

OTHER PUBLICATIONS

English Abstract of DE 10333956.

(Continued)

*Primary Examiner* — Jonathan W Miles
*Assistant Examiner* — Chima Igboko
(74) *Attorney, Agent, or Firm* — Preston Smirman; Smirman IP Law, PLLC

(57) ABSTRACT

An optical obturator system is described. The optical obturator system includes a transparent window member provided on a distal tip portion of the obturator shaft, thus permitting the surgeon to visualize the tissue of the patient (e.g., via an imaging system positioned near the window member). One or more major portions of the optical obturator system may be formed of a biocompatible material, such as but not limited to stainless steel. Accordingly, the optical obturator system may be reusable for a relatively large number of surgical procedures.

14 Claims, 22 Drawing Sheets

(56) References Cited

U.S. PATENT DOCUMENTS

| | | | |
|---|---|---|---|
| 5,334,150 | A | 8/1994 | Kaali |
| 5,364,372 | A | 11/1994 | Danks et al. |
| 5,366,445 | A | 11/1994 | Haber et al. |
| 5,376,076 | A | 12/1994 | Kaali |
| 5,380,291 | A | 1/1995 | Kaali |
| 5,385,572 | A | 1/1995 | Nobles et al. |
| 5,387,196 | A | 2/1995 | Green et al. |
| 5,387,197 | A | 2/1995 | Smith et al. |
| 5,441,041 | A | 8/1995 | Sauer et al. |
| 5,449,370 | A | 9/1995 | Vaitekunas |
| 5,467,762 | A * | 11/1995 | Sauer .................. A61B 17/34 600/105 |
| 5,499,625 | A | 3/1996 | Frass et al. |
| 5,545,150 | A | 8/1996 | Danks et al. |
| 5,569,160 | A | 10/1996 | Sauer et al. |
| 5,569,291 | A | 10/1996 | Privitera et al. |
| 5,569,292 | A | 10/1996 | Schwemberger et al. |
| 5,591,192 | A | 1/1997 | Privitera et al. |
| 5,603,702 | A | 2/1997 | Smith et al. |
| 5,607,440 | A | 3/1997 | Danks et al. |
| 5,620,456 | A | 4/1997 | Sauer et al. |
| 5,658,236 | A | 8/1997 | Sauer et al. |
| 5,685,820 | A * | 11/1997 | Riek .................. A61B 1/00165 600/104 |
| 5,697,913 | A | 12/1997 | Sierocuk et al. |
| 5,709,671 | A | 1/1998 | Stephens et al. |
| 5,738,628 | A * | 4/1998 | Sierocuk ............ A61B 17/3421 600/104 |
| 5,797,943 | A | 8/1998 | Danks et al. |
| 5,817,061 | A * | 10/1998 | Goodwin ............ A61B 17/3417 600/121 |
| 5,860,996 | A | 1/1999 | Urban et al. |
| 5,868,714 | A | 2/1999 | Danks |
| 5,895,377 | A | 4/1999 | Smith et al. |
| 5,904,699 | A | 5/1999 | Schwemberger et al. |
| 5,916,232 | A | 6/1999 | Hart |
| 5,957,888 | A | 9/1999 | Hinchliffe |
| 5,957,947 | A | 9/1999 | Wattiez et al. |
| 5,980,493 | A | 11/1999 | Smith et al. |
| 5,984,908 | A | 11/1999 | Davis et al. |
| 6,017,356 | A | 1/2000 | Frederick et al. |
| 6,063,099 | A | 5/2000 | Danks et al. |
| 6,228,061 | B1 | 5/2001 | Flatland et al. |
| 6,319,266 | B1 | 11/2001 | Stellon et al. |
| 6,371,967 | B1 | 4/2002 | Long et al. |
| 6,471,638 | B1 * | 10/2002 | Chang .................. A61B 1/04 600/104 |
| 6,630,947 | B1 * | 10/2003 | Lieberman .......... E21B 47/0002 348/85 |
| 6,656,198 | B2 | 12/2003 | Tsonton et al. |
| 6,666,846 | B1 | 12/2003 | Turovskiy et al. |
| 6,685,630 | B2 | 2/2004 | Sauer et al. |
| 6,702,787 | B2 | 3/2004 | Racenet et al. |
| 6,923,783 | B2 | 8/2005 | Pasqualucci |
| 7,025,747 | B2 | 4/2006 | Smith |
| D542,918 | S | 5/2007 | Albrecht et al. |
| 7,320,694 | B2 | 1/2008 | O'Heeron |
| 7,322,933 | B2 | 1/2008 | Sauer et al. |
| 7,367,960 | B2 | 5/2008 | Stellon et al. |
| 7,384,423 | B1 * | 6/2008 | Chin ................ A61B 17/00008 606/190 |
| 7,470,230 | B2 * | 12/2008 | Smith .................. A61B 17/34 600/184 |
| 7,559,918 | B2 | 7/2009 | Pasqualucci |
| 7,585,288 | B2 | 9/2009 | Haberland |
| 7,597,701 | B2 | 10/2009 | Hueil et al. |
| 7,637,896 | B2 | 12/2009 | Voegele et al. |
| 7,686,823 | B2 | 3/2010 | Pingleton et al. |
| 7,722,570 | B2 | 5/2010 | Almond et al. |
| 7,758,603 | B2 | 7/2010 | Taylor et al. |
| 7,794,644 | B2 | 9/2010 | Taylor et al. |
| 7,824,327 | B2 | 11/2010 | Smith |
| 7,918,826 | B2 | 4/2011 | Armstrong et al. |
| 7,947,058 | B2 | 5/2011 | Kahle et al. |
| 7,967,791 | B2 | 6/2011 | Franer et al. |
| 8,202,290 | B2 * | 6/2012 | Smith .............. A61B 17/32093 606/185 |
| 2002/0072713 | A1 | 6/2002 | Almond et al. |
| 2002/0183775 | A1 * | 12/2002 | Tsonton ............. A61B 17/3417 606/185 |
| 2005/0070850 | A1 | 3/2005 | Albrecht |
| 2005/0070947 | A1 | 3/2005 | Franer et al. |
| 2005/0149096 | A1 | 7/2005 | Hilal et al. |
| 2005/0203559 | A1 | 9/2005 | O'Heeron |
| 2006/0173479 | A1 * | 8/2006 | Smith ................ A61B 1/00135 606/185 |
| 2006/0264992 | A1 | 11/2006 | Franer et al. |
| 2007/0010842 | A1 | 1/2007 | Popov |
| 2007/0088277 | A1 | 4/2007 | McGinley et al. |
| 2007/0093851 | A1 | 4/2007 | Moran et al. |
| 2007/0129719 | A1 * | 6/2007 | Kendale ............ A61B 1/00096 606/41 |
| 2007/0185453 | A1 | 8/2007 | Michael et al. |
| 2007/0260273 | A1 * | 11/2007 | Cropper ............ A61B 1/00087 606/185 |
| 2007/0260275 | A1 | 11/2007 | Ahlberg et al. |
| 2008/0051735 | A1 | 2/2008 | Measamer et al. |
| 2008/0086074 | A1 | 4/2008 | Taylor et al. |
| 2008/0103439 | A1 * | 5/2008 | Torrance ............ A61B 17/3207 604/93.01 |
| 2008/0215033 | A1 * | 9/2008 | Miller ................ A61B 17/3478 604/509 |
| 2008/0294184 | A1 * | 11/2008 | Smith ................ A61B 17/3417 606/185 |
| 2009/0069806 | A1 * | 3/2009 | De La Mora Levy .................. A61B 17/221 606/46 |
| 2009/0076323 | A1 | 3/2009 | Smith et al. |
| 2009/0093833 | A1 | 4/2009 | Smith |
| 2009/0177030 | A1 * | 7/2009 | Goto ................ A61B 17/32002 600/104 |
| 2009/0270817 | A1 | 10/2009 | Moreno et al. |
| 2009/0281376 | A1 | 11/2009 | Acosta et al. |
| 2009/0281386 | A1 | 11/2009 | Acosta et al. |
| 2009/0281498 | A1 | 11/2009 | Acosta et al. |
| 2009/0281500 | A1 | 11/2009 | Acosta et al. |
| 2009/0306698 | A1 * | 12/2009 | Mayenberger ..... A61B 17/3417 606/185 |
| 2010/0016664 | A1 | 1/2010 | Viola |
| 2010/0022959 | A1 | 1/2010 | Moran et al. |
| 2010/0053312 | A1 * | 3/2010 | Watanabe .......... A61B 1/00096 348/65 |
| 2010/0081988 | A1 * | 4/2010 | Kahle ................ A61B 17/3417 604/26 |
| 2010/0137895 | A1 | 6/2010 | Smith |
| 2011/0257646 | A1 * | 10/2011 | Utley .................. A61B 18/149 606/33 |

FOREIGN PATENT DOCUMENTS

| | | |
|---|---|---|
| EP | 1707132 | 10/2006 |
| JP | 7250810 | 10/1995 |

OTHER PUBLICATIONS

English Abstract of JP 7250810.

* cited by examiner

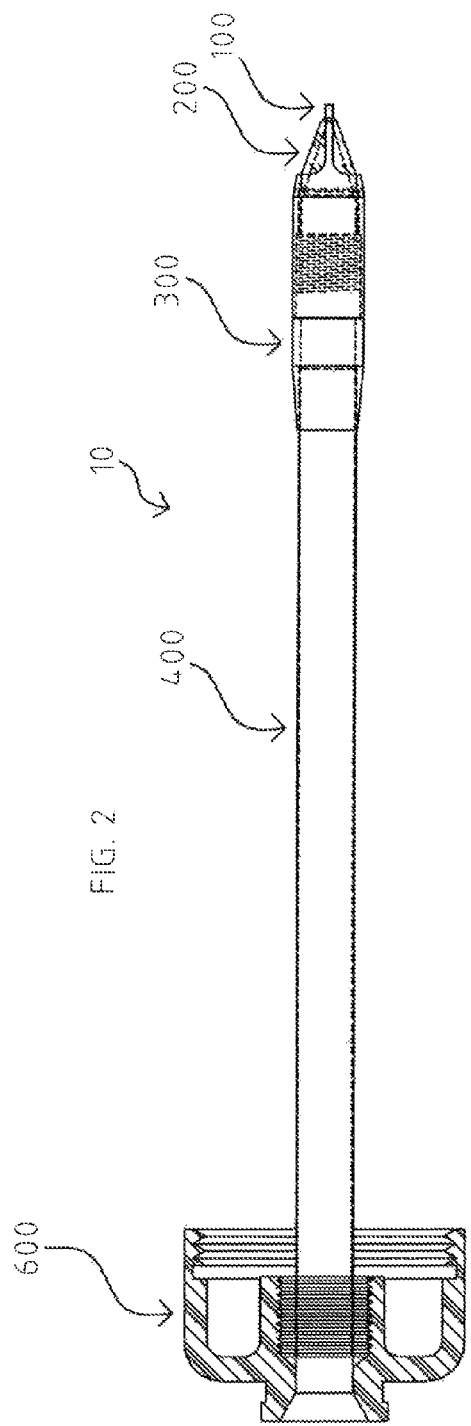
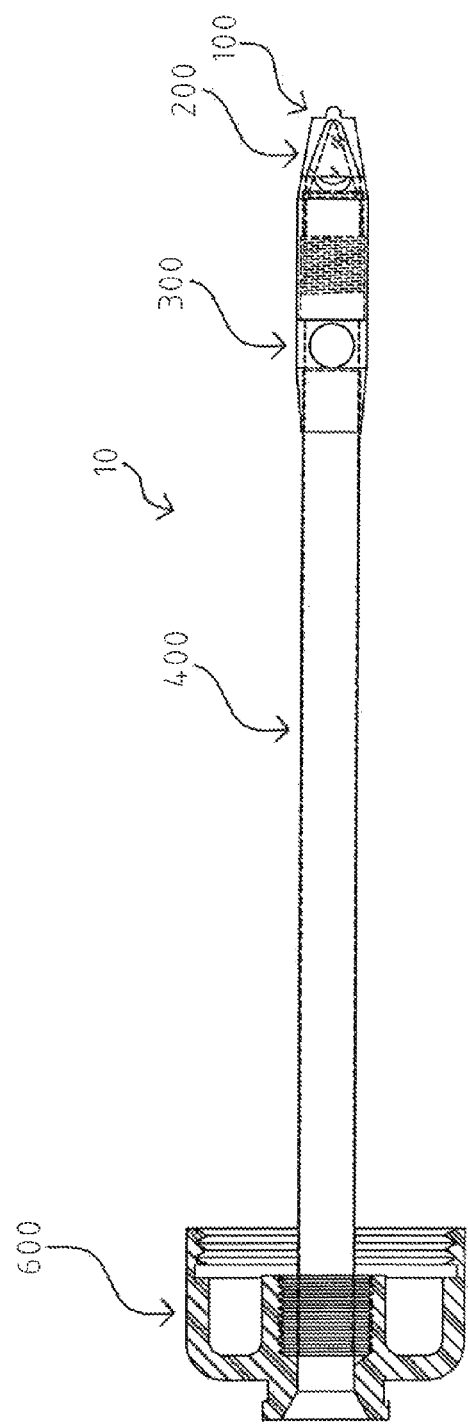

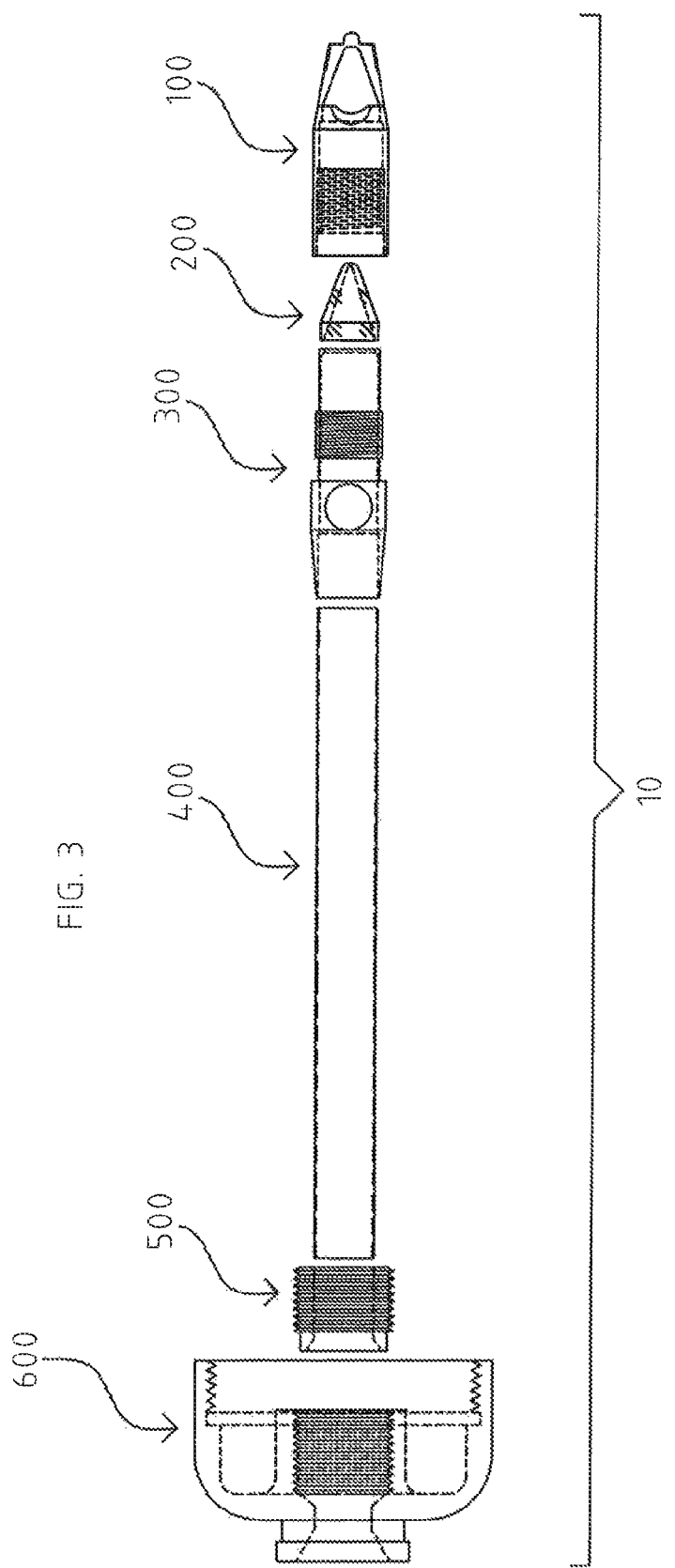

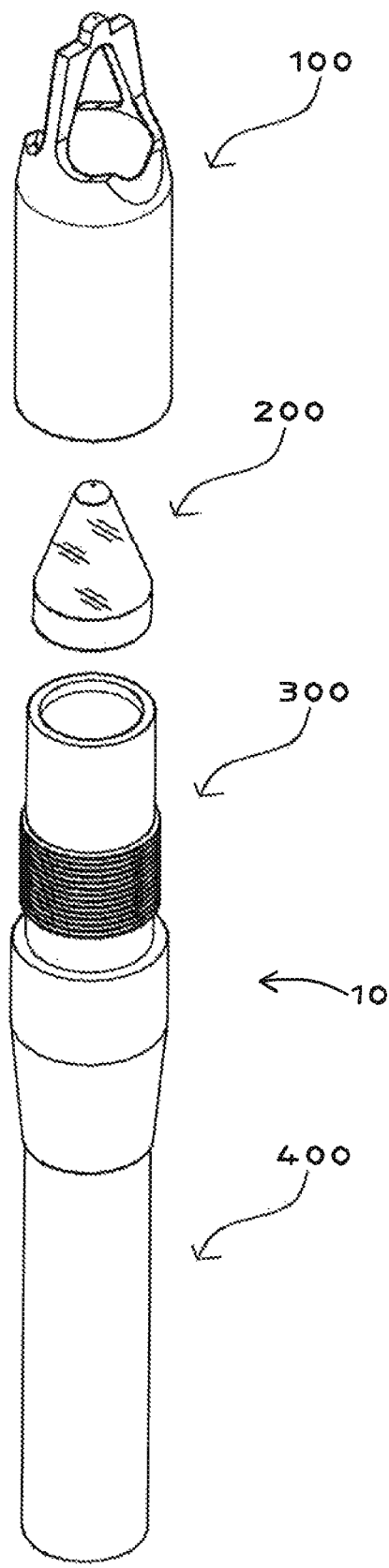

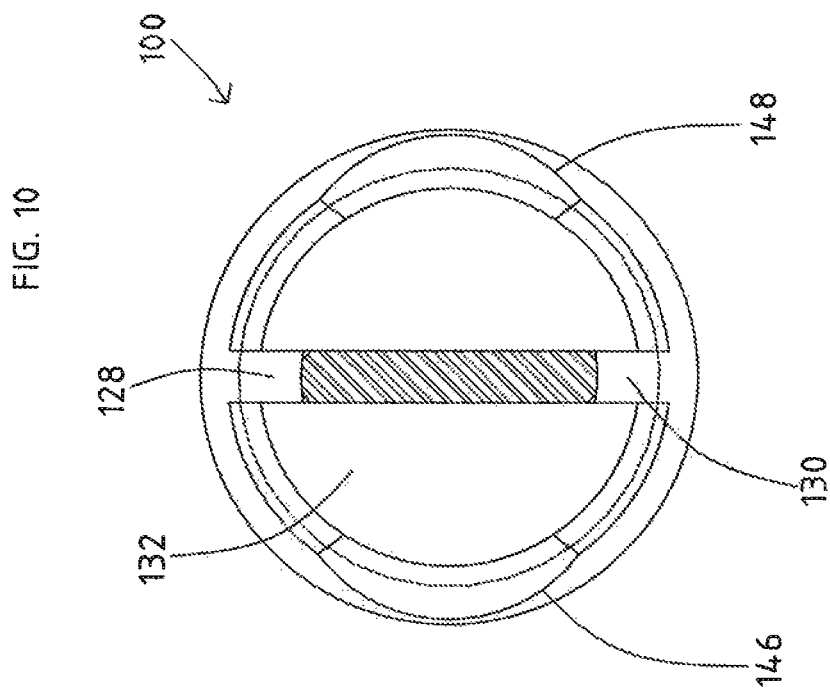

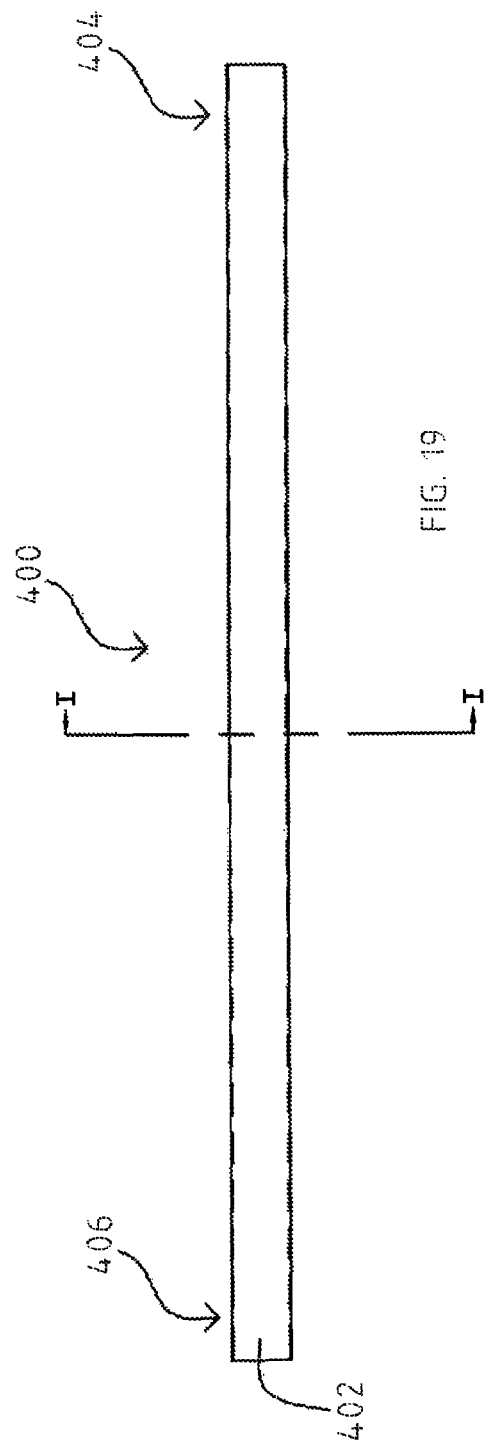
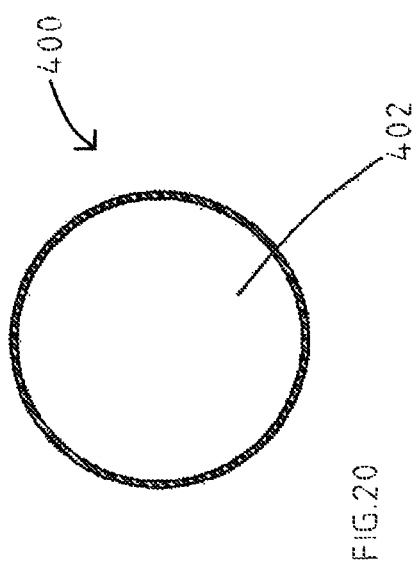
FIG. 19
FIG. 20

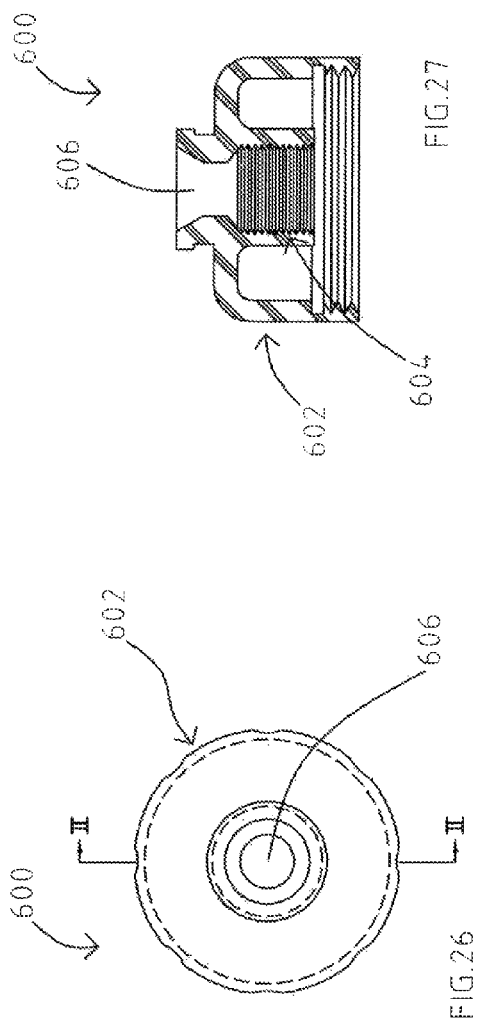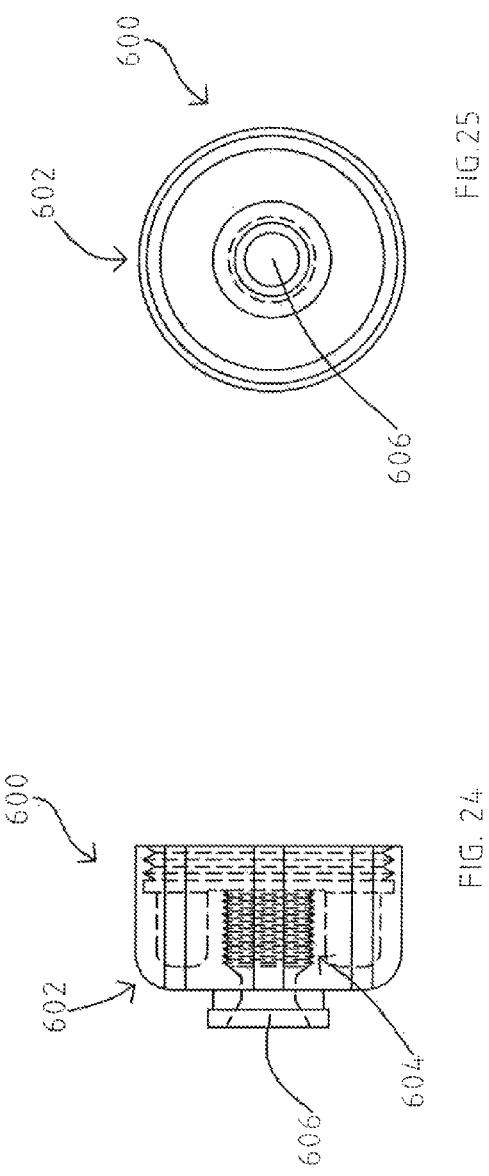

OPTICAL OBTURATOR SYSTEM

CROSS-REFERENCE TO RELATED APPLICATION

The instant application claims priority to U.S. Provisional Patent Application Ser. No. 61/639,225, filed Apr. 27, 2012, the entire specification of which is expressly incorporated herein by reference.

FIELD OF INVENTION

The present invention relates generally to obturators and more specifically to reusable optical obturator systems with a transparent window member provided on a distal tip portion of the obturator shaft, and methods for making the same.

BACKGROUND OF THE INVENTION

Endoscopy, and especially laparoscopic endoscopy, has been a rapidly growing surgical practice in the past decades. Accessing the patient's laparoscopic cavity is typically done via holes, usually punctured with a sharp element referred to as either a trocar or obturator. In order to penetrate the patient's laparoscopic cavity, the obturator is placed into a tubular element referred to as a cannula, such that the sharp end of the obturator is protruding from the cannula's distal end. The obturator end, when sharp, may puncture the abdominal wall. When an obturator is used, an initial incision to the patient's skin is typically required. Once the cavity has been penetrated by the obturator, it can be withdrawn and various surgical instruments may then be introduced through the cannula and into the typically insufflated cavity.

A recent development in the obturator art has been the so-called "optical obturator" which provides a means for permitting the surgeon to visualize the specific area of the patient's tissue that the tip or distal portion of the obturator is proximate to and/or actually engaging. Typically, this capability is provided by a transparent window portion being provided on, or very near, the distal portion of the obturator. However, a major disadvantage of conventional optical obturators is that they are most commonly suitable for only single patient use, that is, the entire optical obturator assembly and/or major portions thereof, are difficult, if not impossible, to adequately sterilize without a resulting degradation of either the structure and/or performance thereof. Even those conventional optical obturators that may be suitable for reposable uses (i.e., suitable for a relatively low number of surgical uses) and/or reusable uses (i.e., suitable for a relatively high number of surgical uses), they are nonetheless generally very difficult to manufacture and/or are very expensive to produce.

Accordingly, there exists a need for new and improved reusable optical obturators, and methods for making the same.

SUMMARY OF THE INVENTION

In accordance with the general teachings of the present invention, an optical obturator system is provided. The optical obturator system allows for penetration into the patient's laparoscopic cavity and also permits visualization, e.g., by the surgeon, of the patient's tissues via a transparent window member provided on a distal tip portion of the obturator shaft (e.g., via an imaging system positioned near the window member). One or more major portions of the optical obturator system may be formed of a biocompatible material, such as but not limited to stainless steel. Accordingly, the optical obturator system, or at least major portions thereof, is reusable for a relatively large number of surgical procedures, assuming conventional sterilization techniques are employed after each surgical procedure.

Methods for forming the optical obturator system are also provided.

In accordance with a first embodiment of the present invention, an optical obturator system is provided, comprising:

a tip member having a proximal portion and a distal portion;

wherein the proximal portion includes a substantially cylindrically shaped body including an area defining an open end and an annular wall member defining a bore extending therefrom towards the distal portion, wherein a threaded portion is formed on a portion of a first wall surface of the bore;

wherein the distal portion includes a pair of tapered arm members that define a cavity, wherein the cavity communicates with the bore, wherein the arm members are joined together at a distal portion to provide a substantially conical surface, wherein a rounded blunt surface is formed on a terminus of the distal portion, wherein one or more cutting surfaces are formed on an edge surface of the arm members, wherein one or more areas defining a curved aperture are formed in a body of the distal portion; and a transparent window member having a proximal portion and a distal portion;

wherein the proximal portion includes a circular annular surface;

wherein the distal portion includes a conical portion, wherein a surface thereof tapers towards a rounded terminus, wherein an area defining a cavity is formed in the proximal portion and extends into the conical portion proximate to the terminus;

wherein the transparent window member is configured so as to be operable to be at least partially received within the cavity of the tip member and held in place by the arm members.

In accordance with a second embodiment of the present invention, an optical obturator system is provided, comprising:

a tip member having a proximal portion and a distal portion;

wherein the proximal portion includes a substantially cylindrically shaped body including an area defining an open end and an annular wall member defining a bore extending therefrom towards the distal portion, wherein a threaded portion is formed on a portion of a first wall surface of the bore;

wherein the distal portion includes a pair of tapered arm members that define a cavity, wherein the cavity communicates with the bore, wherein the arm members are joined together at a distal portion to provide a substantially conical surface, wherein a rounded blunt surface is formed on a terminus of the distal portion, wherein one or more cutting surfaces are formed on an edge surface of the arm members, wherein one or more areas defining a curved aperture are formed in a body of the distal portion;

a transparent window member having a proximal portion and a distal portion;

wherein the proximal portion includes a circular annular surface;

wherein the distal portion includes a conical portion, wherein a surface thereof tapers towards a rounded terminus, wherein an area defining a cavity is formed in the proximal portion and extends into the conical portion proximate to the terminus;

wherein the transparent window member is configured so as to be operable to be at least partially received within the cavity of the tip member and held in place by the arm members; and a retainer member selectively operable to secure the transparent window member in the tip member so as to prevent any relative movement therebetween;

wherein the retainer member includes a proximal portion and a distal portion;

wherein the distal portion includes a body member with a threaded surface formed on a portion thereof;

wherein the retainer member and the tip member are selectively operable to be brought into engagement such that the distal portion of the retainer member is received in the bore of the tip member, such that the threaded surface of the tip member and the threaded surface of the retainer member are brought into threaded engagement with one another.

In accordance with a third embodiment of the present invention, an optical obturator system is provided, comprising:

a tip member having a proximal portion and a distal portion;

wherein the proximal portion includes a substantially cylindrically shaped body including an area defining an open end and an annular wall member defining a bore extending therefrom towards the distal portion, wherein a threaded portion is formed on a portion of a first wall surface of the bore, wherein a portion of the first wall surface includes an area defining an annular shoulder in proximity to the proximal portion of the threaded portion and further defines a second wall surface of increased diameter as compared to that of the first wall surface;

wherein the distal portion includes a pair of tapered arm members that define a cavity, wherein the cavity communicates with the bore, wherein the arm members are joined together at a distal portion to provide a substantially conical surface, wherein a rounded blunt surface is formed on a terminus of the distal portion, wherein one or more cutting surfaces are formed on an edge surface of the arm members, wherein one or more areas defining a curved aperture are formed in a body of the distal portion, wherein the distal portion includes a third wall surface having a decreased diameter as compared to that of either the first wall surface or the second wall surface such that a shoulder is defined between the first wall surface and the third wall surface;

a transparent window member having a proximal portion and a distal portion;

wherein the proximal portion includes a circular annular surface;

wherein the distal portion includes a conical portion, wherein a surface thereof tapers towards a rounded terminus, wherein an area defining a cavity is formed in the proximal portion and extends into the conical portion proximate to the terminus;

wherein the proximal portion of the transparent window member has a diameter that is configured so as to allow the transparent window member to pass through the bore of the tip member and past the first, second and third wall surfaces;

wherein the transparent window member is configured so as to be operable to be at least partially received within the cavity of the tip member and held in place by the arm members; and a retainer member selectively operable to secure the transparent window member in the tip member so as to prevent any relative movement therebetween;

wherein the retainer member includes a proximal portion and a distal portion;

wherein the proximal portion includes an open end and a tapered annular wall surface defining a bore that extends completely through to the distal portion, wherein the annular wall surface includes an area defining an internal annular shoulder surface, wherein at an opposed end of the annular wall surface there is an area defining an external annular shoulder surface;

wherein the distal portion includes a body member with a threaded surface formed on a portion thereof, wherein at an end of the body member there is formed an annular shoulder surface formed on an internal surface of the bore;

wherein the retainer member and the tip member are selectively operable to be brought into engagement such that the distal portion of the retainer member is received in the bore of the tip member, such that the threaded surface of the tip member and the threaded surface of the retainer member are brought into threaded engagement with one another.

Further areas of applicability of the present invention will become apparent from the detailed description provided hereinafter. It should be understood that the detailed description and specific examples, while indicating the preferred embodiment of the invention, are intended for purposed of illustration only and are not intended to limit the scope of the invention.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 illustrates an elevational view of an optical obturator system, in accordance with a first embodiment of the present invention;

FIG. 2 illustrates a side view of an optical obturator system, in accordance with a second embodiment of the present invention;

FIG. 3 illustrates an exploded view of an optical obturator system, in accordance with a third embodiment of the present invention;

FIG. 4 illustrates a partial exploded view of a distal portion of an optical obturator system, in accordance with a fourth embodiment of the present invention;

FIG. 10 illustrates a partial sectional view of the tip member depicted in FIG. 7, in accordance with a tenth embodiment of the present invention;

FIG. 19 illustrates an elevational view of a shaft member of an optical obturator system, in accordance with a nineteenth embodiment of the present invention;

FIG. 20 illustrates a sectional view taken along line I-I of FIG. 19, in accordance with a twentieth embodiment of the present invention;

FIG. 24 illustrates an elevational view of a handle member of an optical obturator system, in accordance with a twenty-fourth embodiment of the present invention;

FIG. 25 illustrates a top plan view of a handle member of an optical obturator system, in accordance with a twenty-fifth embodiment of the present invention;

FIG. 26 illustrates a bottom plan view of a handle member of an optical obturator system, in accordance with a twenty-sixth embodiment of the present invention;

FIG. 27 illustrates a sectional view taken along line II-II of FIG. 26, in accordance with a twenty-seventh embodiment of the present invention;

The same reference numerals refer to the same parts throughout the various Figures.

DETAILED DESCRIPTION OF THE INVENTION

Figure 5:
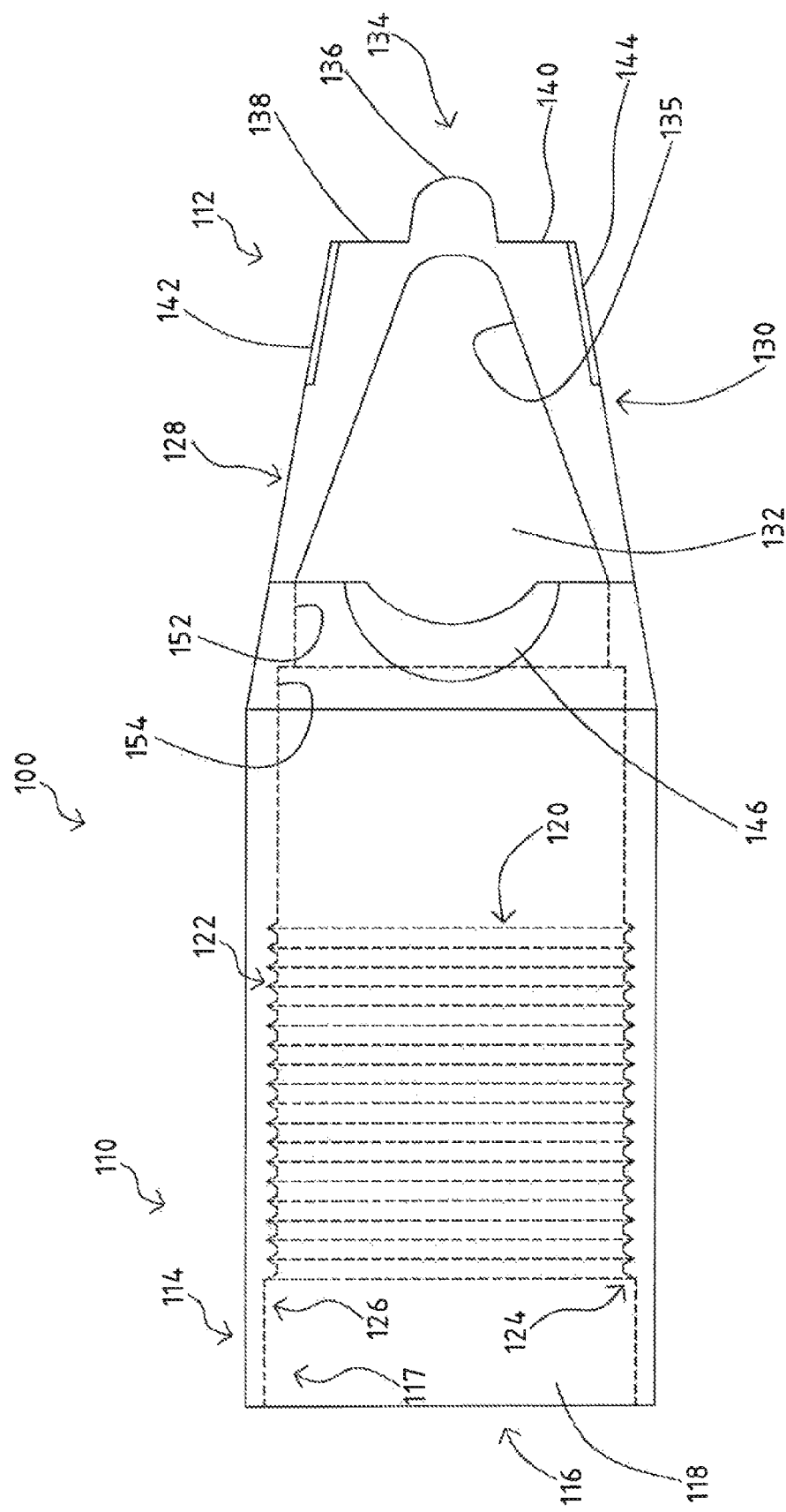
FIG. 5 illustrates an elevational view of a tip member of an optical obturator system, in accordance with a fifth embodiment of the present invention.
Figure 6:
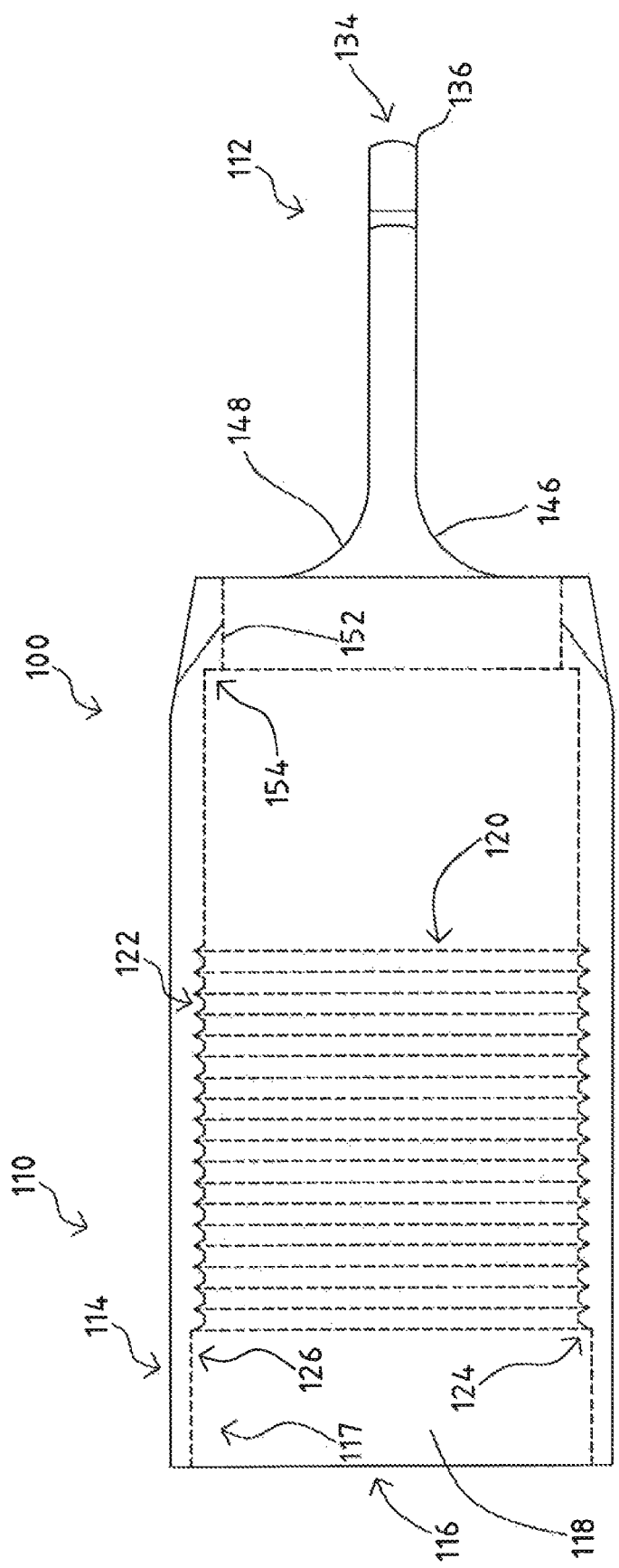
FIG. 6 illustrates a side elevational view of a tip member of an optical obturator system, in accordance with a sixth embodiment of the present invention.
Figure 7:
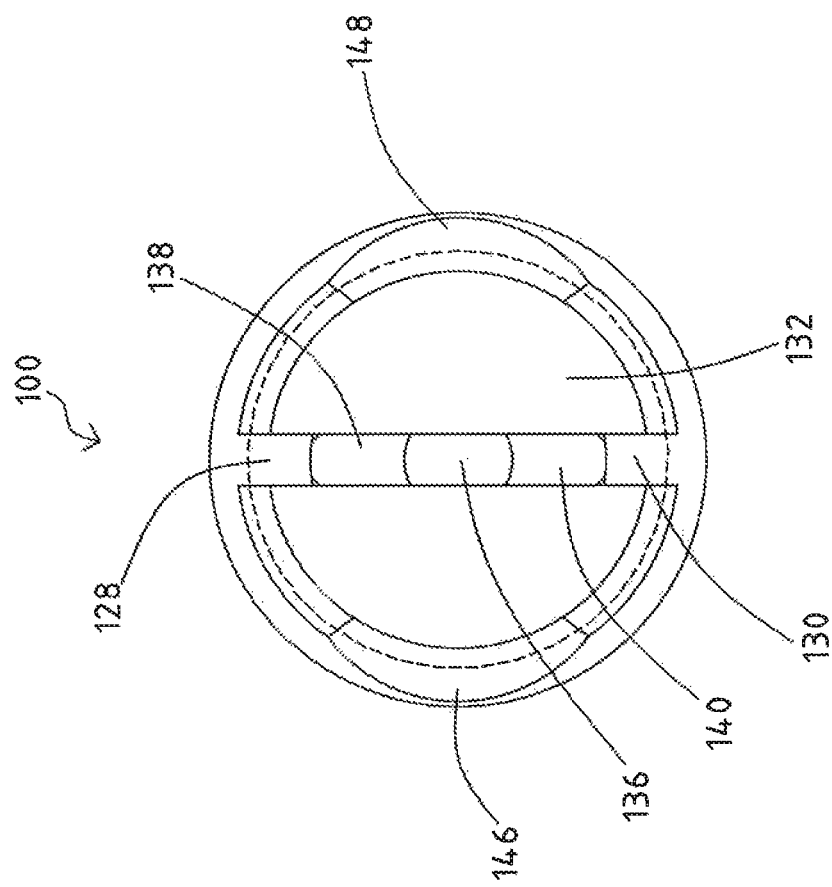
FIG. 7 illustrates a bottom plan view of a tip member of an optical obturator system, in accordance with a seventh embodiment of the present invention.
Figure 8:
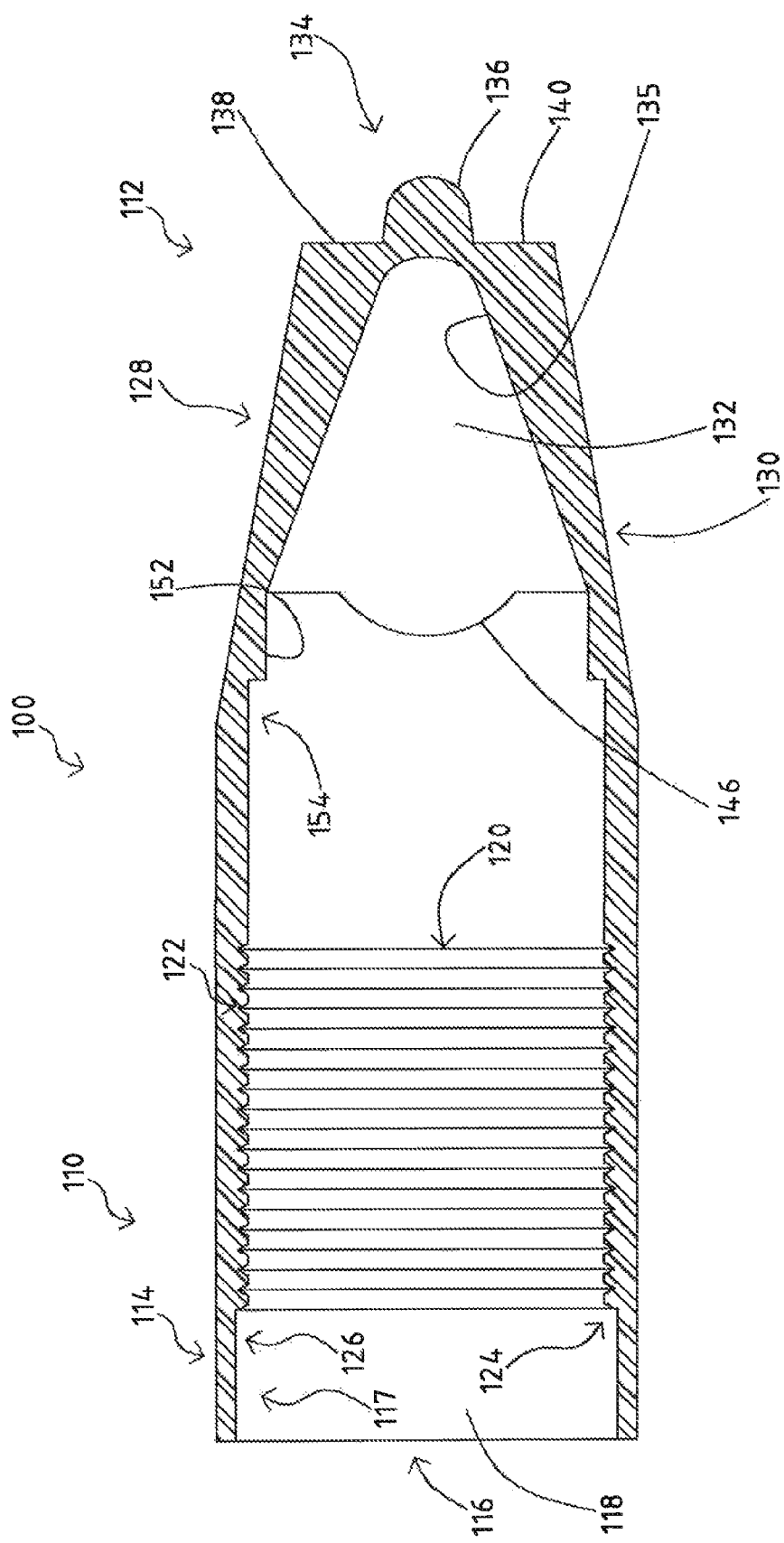
FIG. 8 illustrates a sectional view of the tip member depicted in FIG. 5, in accordance with an eighth embodiment of the present invention.
Figure 9:
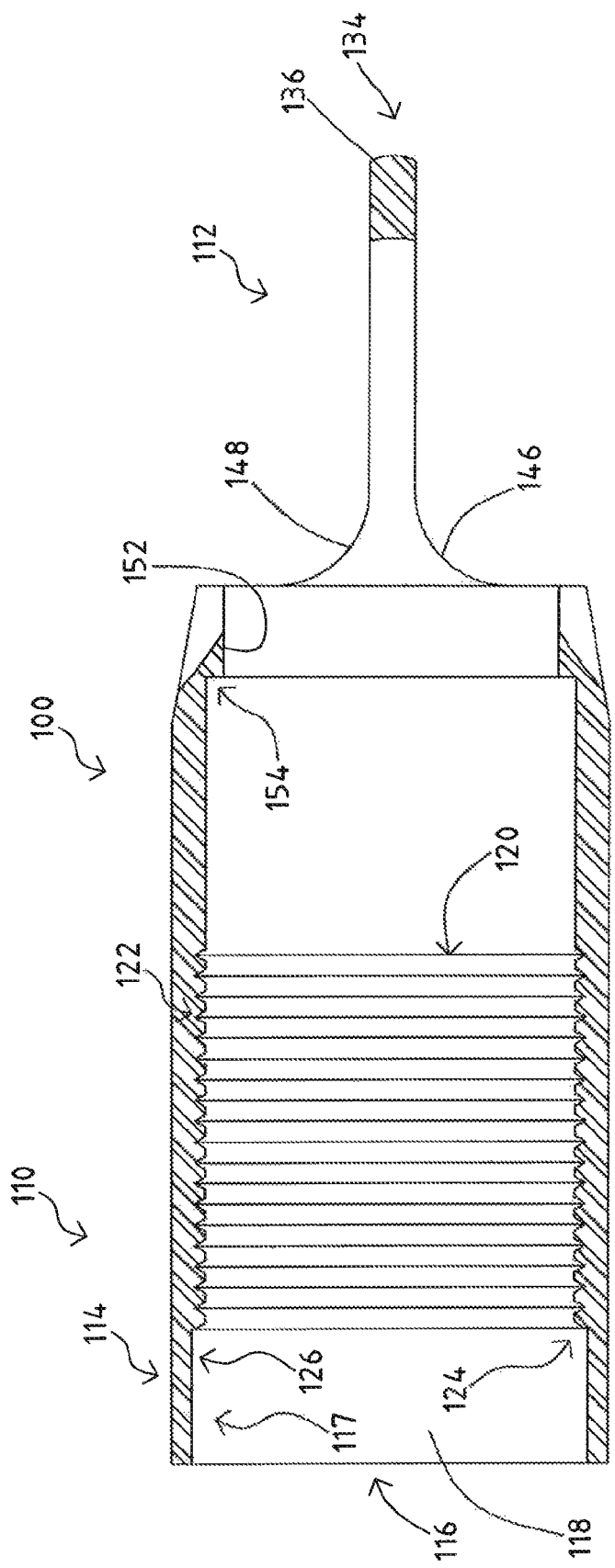
FIG. 9 illustrates a sectional view of the tip member depicted in FIG. 6, in accordance with a ninth embodiment of the present invention.
Figure 12:
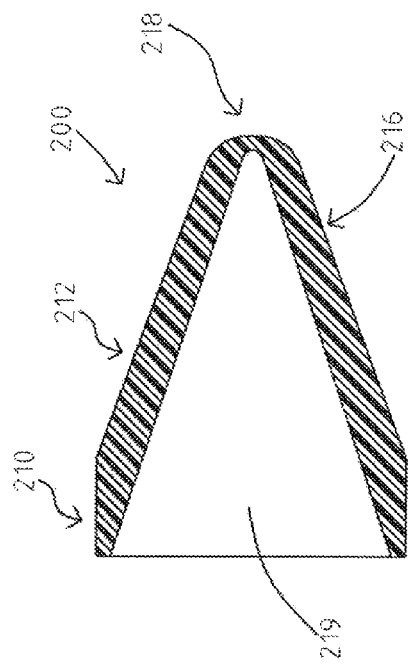
FIG. 12 illustrates a sectional view of a transparent window member of an optical obturator system, in accordance with a twelfth embodiment of the present invention.
Figure 14:
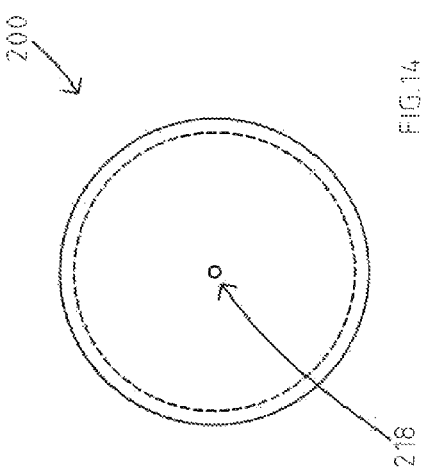
FIG. 14 illustrates a bottom plan view of a transparent window member of an optical obturator system, in accordance with a fourteenth embodiment of the present invention.
Figure 13:
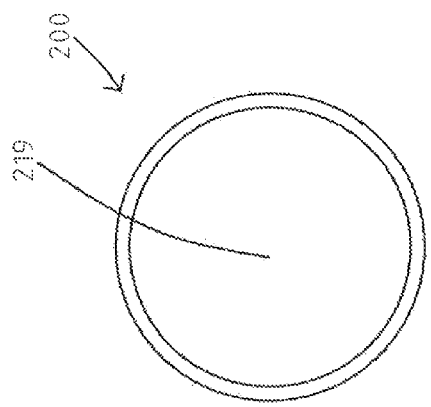
FIG. 13 illustrates a top plan view of a transparent window member of an optical obturator system, in accordance with a thirteenth embodiment of the present invention.
Figure 11:
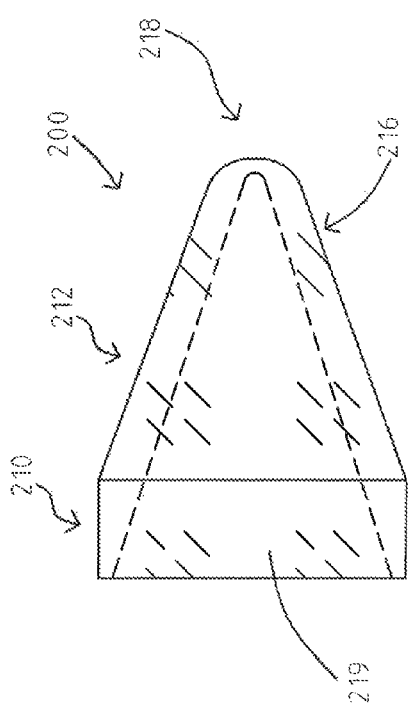
FIG. 11 illustrates an elevational view of a transparent window member of an optical obturator system, in accordance with an eleventh embodiment of the present invention.
Figure 15:
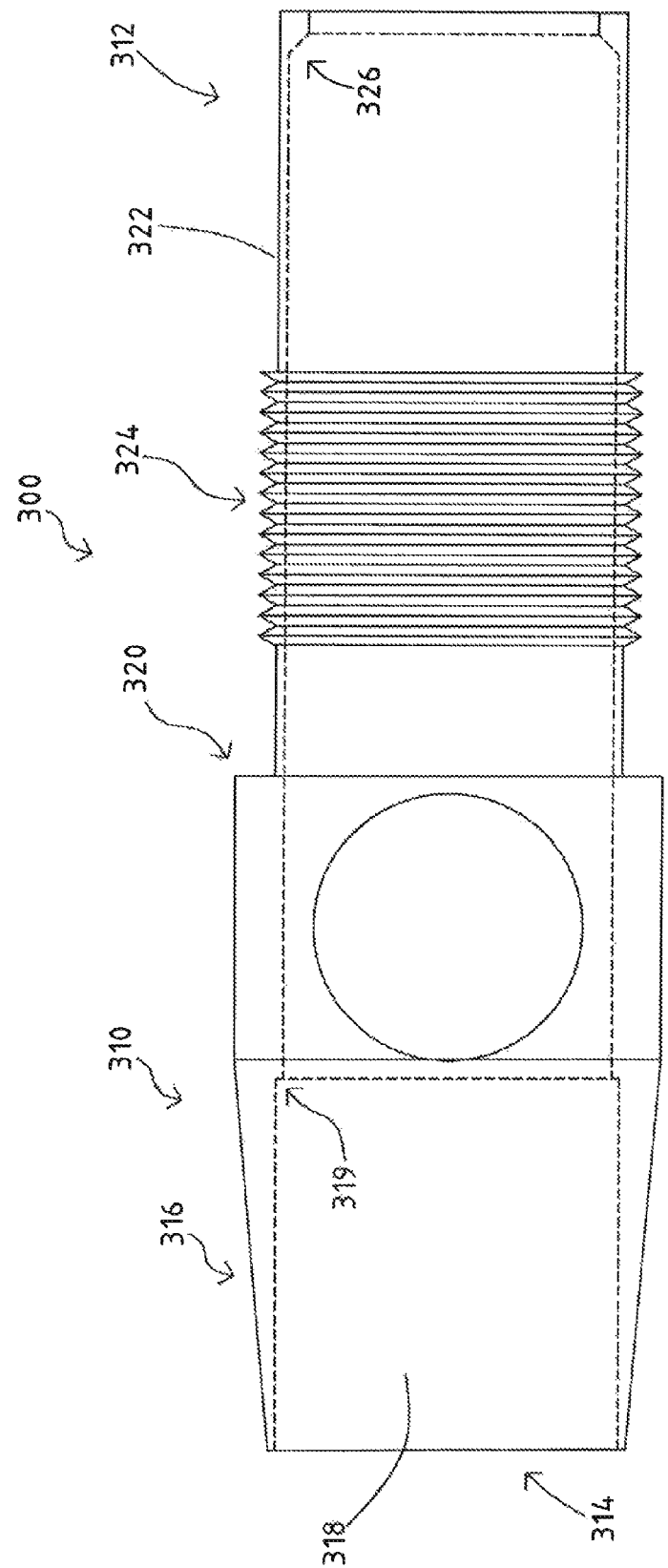
FIG. 15 illustrates an elevational view of a retainer member of an optical obturator system, in accordance with a fifteenth embodiment of the present invention.
Figure 16:
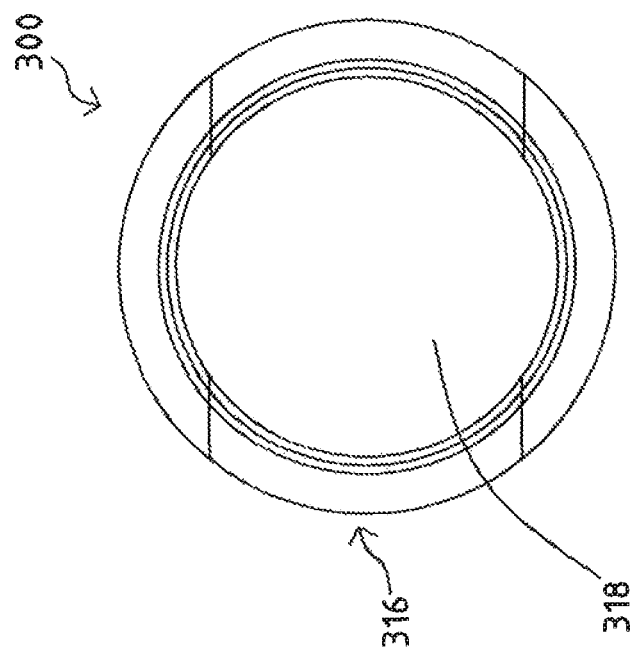
FIG. 16 illustrates a top plan view of a retainer member of an optical obturator system, in accordance with a sixteenth embodiment of the present invention.
Figure 17:
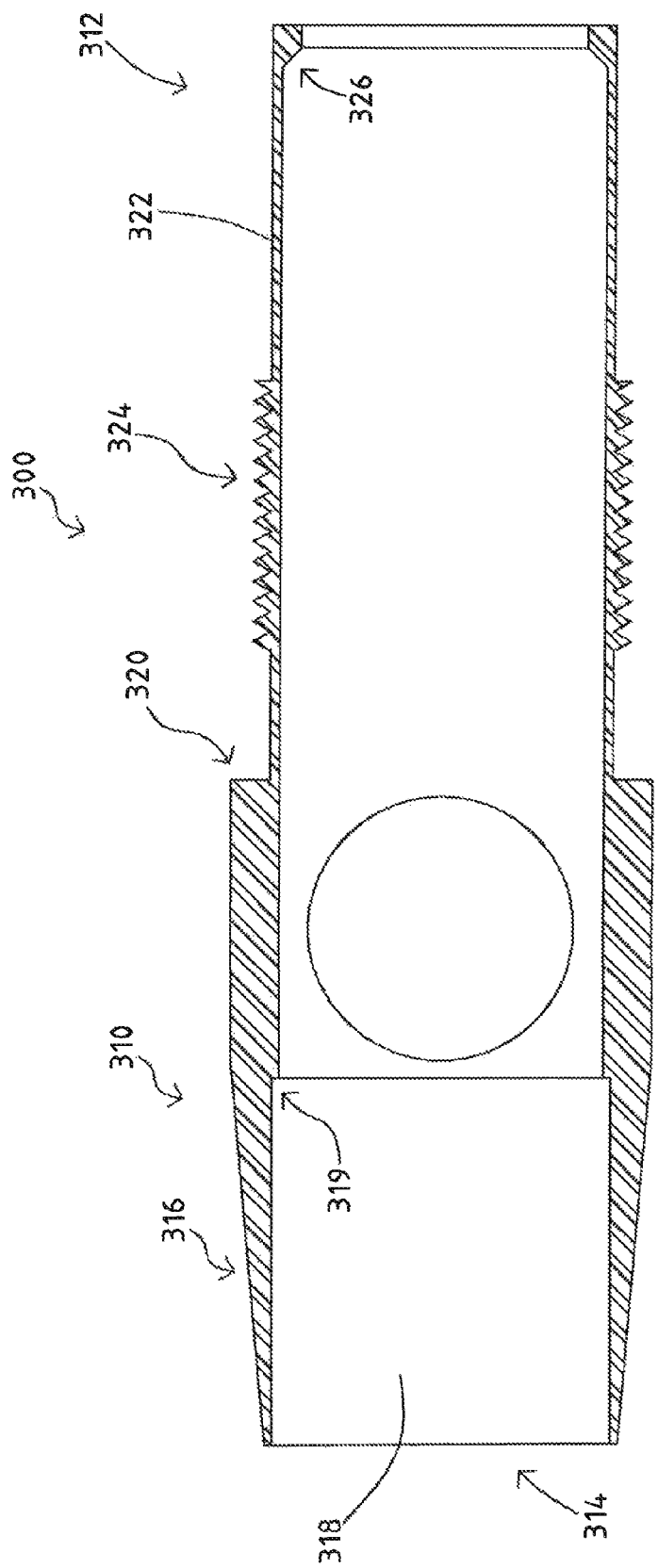
FIG. 17 illustrates a sectional view of the retainer member depicted in FIG. 15, in accordance with a seventeenth embodiment of the present invention.
Figure 18:
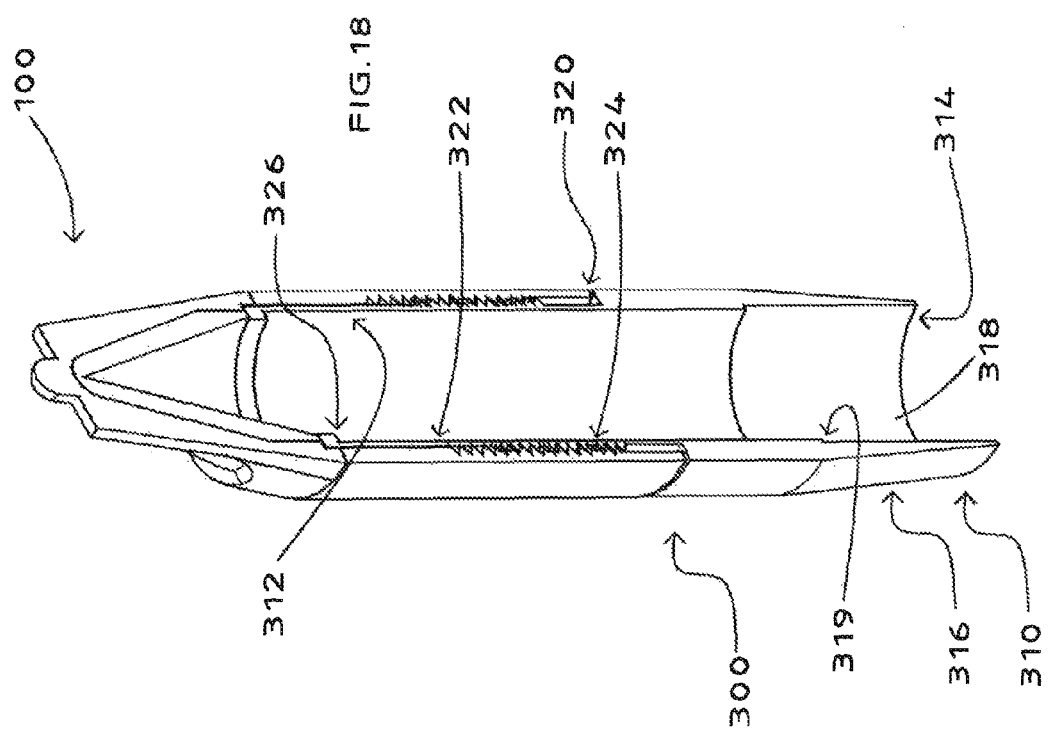
FIG. 18 illustrates a torn away view of a tip member/retainer member assembly, in accordance with an eighteenth embodiment of the present invention.

The following description of the preferred embodiment(s) is merely exemplary in nature and is in no way intended to limit the invention, or uses.

Referring to the drawings generally, and specifically to FIGS. 1-4, there is shown an optical obturator system generally at 10. The optical obturator system 10 primarily includes a tip member 100, a transparent window member 200, a retainer member 300, a shaft member 400, a connector member 500, and a handle member 600. It should be appreciated that the optical obturator system 10 of the present invention may be operable to interoperate with a cannula or similar device during a surgical procedure.

Referring to the drawings generally, and specifically to FIGS. 5-10, there are shown several views of the tip member 100. The tip member 100 may include a proximal portion 110 and a distal portion 112.

The proximal portion 110 may include a substantially cylindrically shaped body 114 including an open end 116 and an annular wall member 117 defining a bore 118 extending therefrom towards the distal portion 112. A threaded portion 120 may be formed on a portion of a wall surface 122 of the bore 118. A portion of the wall surface 122 may include an area defining an annular shoulder 124 in proximity to the proximal portion of the threaded portion 120, and may further define a wall surface 126 of increased diameter as compared to that of the wall surface 122.

The distal portion 112 may include a pair of tapered arm members 128, 130, respectively, that may define a cavity 132. The cavity 132 may communicate with the bore 118 such that an object, e.g., the transparent window member 200, may be introduced into the open end 116 of the bore 118 and be positioned in the cavity 132. The arm member 128, 130, respectively, may be joined or otherwise formed together at a distal portion 134 to provide a substantially conical surface 135. By way of a non-limiting example, excess material may be removed (e.g., by grinding, etching, and/or the like) from the distal portion 112 to form and/or define the cavity 132 and/or the arm members, 128, 130, respectively, e.g., to include the desired taper profile.

A rounded or semi-hemispherical blunt surface 136 may be formed on the terminus of the distal portion 134, e.g., to prevent unintended penetration of the patient's tissues. One or more cutting surfaces 138, 140, 142, 144, respectively, may be formed on the edge surfaces of the arm member 128, 130, respectively. Optionally, one or more areas defining a curved, arcuate or scallop-shaped aperture 146, 148, respectively, may be formed in the body 150 of the distal portion 112 to permit enhanced viewing capability, e.g., at 90 degrees perpendicular to the respective cutting surfaces. The cutting surfaces may be selectively operable to cut through various bodily tissues so as to penetrate a patient's bodily cavities. That is, the cutting surfaces may be formed with areas of sufficient sharpness so as to penetrate and cut through tissue without undue effort by the surgeon.

The distal portion 112 may also include a wall surface 152 having a decreased diameter as compared to that of either the wall surface 122 or wall surface 126. In this manner, a shoulder 154 may be defined between wall surface 152 and wall surface 122.

The tip member 100 may be comprised of a biocompatible material, such as but not limited to stainless steel. The chosen material is preferably suitable to be sterilized by conventional methods numerous times without any appreciable degradation or loss of function.

Referring to the drawings generally, and specifically to FIGS. 11-14, there are shown several views of the transparent window member 200. The transparent window member 200 may include a proximal portion 210 and a distal portion 212.

The proximal portion 210 may include a circular annular surface 214. The distal portion 212 may include a conical portion 216, wherein the surfaces thereof may taper towards a rounded or blunt terminus 218. An area defining a hollow core or cavity 219 may be formed in the proximal portion 210 and may extend into the conical portion 216, e.g., near or proximate to the terminus 218. In accordance with one aspect of the present invention, the cavity 219 may reduce material requirements and/or to permit access of a camera system and/or illumination system closer to the distal portion 212 (e.g., the conical portion 216). In accordance with another aspect of the present invention, the transparent window member 200 may be configured to eliminate any angled surfaces (e.g., 90 degree angles) that might potentially interfere with the ability of the surgeon to clearly view the surgical environment (e.g., the patient's tissues).

The transparent window member 200 may be sized and configured so as to be operable to be at least partially, and more preferably, fully received within the cavity 132 of the tip member 100 and held in place by the arm members, 128, 130, respectively.

By way of a non-limiting example, the diameter of the proximal portion 210, and more specifically the annular surface 214, may be sized so as to allow the transparent window member 200 to pass relatively freely through bore 118 and past wall surfaces 122, 126, and/or 152, respectively.

The transparent window member 200 may be comprised of a biocompatible material, such as but not limited to polycarbonate and/or other suitable plastic materials. The chosen material is preferably suitable to be sterilized by conventional methods numerous times without any appreciable degradation or loss of function. It should be appreciated that although the transparent window member 200 may be reused several times, it may also be suitable for use as a single use component.

In this manner, an imaging system (not shown), such as but not limited to a camera system, illumination system, and/or display system, may be introduced through bore 118 and then into or proximate to the cavity 219 of the transparent window member 200. The imaging system may then be used by the surgeon, or other healthcare personnel, to view the tissue of the patient that is being engaged and/or cut by the optical obturator system 10. In this manner, the surgeon can more easily see the surgical environment (e.g., the patient's tissues) that the optical obturator system 10 is proximate to, and therefore, can ensure that only those tissues that are intended to be engaged are actually engaged.

By way of a non-limiting example, the arm members, 128, 130, respectively, may be sized so as to avoid any diminishment in visibility through the transparent window member 200. By way of a non-limiting example, the arm members, 128, 130, respectively, may be configured as a single piece core with a 0.030 inches wide cutting/dilating surface. By choosing a relatively thin surface diameter for the arm members, 128, 130, respectively, the arm members, 128, 130, respectively, will not be visible through the transparent window member 200, e.g., when the surgeon is viewing the same. By way of a non-limiting example, it is believed that using a diameter greater than 0.030 inches, could cause the arm members, 128, 130, respectively, to be visible in the surgeon's field of view.

Referring to the drawings generally, and specifically to FIGS. 15-18, there are shown several views of the retainer member 300. The intended purpose of the retainer member 300, among other things, is to secure the transparent window member 200 in the tip member 100, specifically the cavity 132, to prevent any unintended relative movement.

The retainer member 300 may include a proximal portion 310 and a distal portion 312.

The proximal portion 310 may include an open end 314 and a tapered annular wall surface 316 defining a bore 318 that extends completely through to the distal portion 312 so as to allow instrumentation to pass there through. The annular wall surface 316 may include an area defining an internal annular shoulder surface 319. At an opposed end of the annular wall surface 316, there may be an area defining an external annular shoulder surface 320.

The distal portion 312 may include a body member 322 with a threaded surface 324 formed on a portion thereof. At the end of the body member 322, there may be formed an annular shoulder surface 326 formed on an internal surface of the bore 318.

The retainer member 300 may be comprised of a biocompatible material, such as but not limited to stainless steel. The chosen material is preferably suitable to be sterilized by conventional methods numerous times without any appreciable degradation or loss of function.

By way of a non-limiting example, the retainer member 300 is intended to engage the tip member 100 so as to retain the transparent window member 200 therein. By way of a non-limiting example, the retainer member 300 and the tip member 100 may be brought into engagement such that the distal portion 314 of the retainer member 300 may be received in the bore 118 of the tip member 100. As this occurs, the threaded surface 120 of the tip member 100 and the threaded surface 324 of the retainer member 300 may be brought into threaded engagement with one another. As the respective threaded surfaces are brought into engagement, relative movement of the tip member 100 and the retainer member 300 may cease when the shoulder surface 326 engages the shoulder 154 and/or the wall member 117 engages the shoulder surface 320. In this manner, the tip member 100 and/or transparent window member 200 may be removed from the retainer member 300 (e.g., via the threaded surface 324 of the retainer member 300) and either sterilized for additional uses and/or replaced by another sterile tip member 100 and/or transparent window member 200, without having to dispose of the other major components of the optical obturator system 10. An adhesive (e.g., temporary and/or permanent) or other suitable material may be used to secure the attachment of the tip member 100 and the retainer member 300. It should be appreciated that the tip member 100 may be removed from the retainer member 300 at a subsequent later time, e.g., for sterilization purposes.

Referring to the drawings generally, and specifically to FIGS. 19-20, there is shown several views of the shaft member 400. In this view, the shaft member 400 is shown as being substantially cylindrical with an area defining a bore 402 extending completely there through so as to allow instrumentation to pass there through.

The shaft member 400 may be comprised of a biocompatible material, such as but not limited to stainless steel. The chosen material is preferably suitable to be sterilized by conventional methods numerous times without any appreciable degradation or loss of function.

By way of a non-limiting example, the proximal portion 310 of the retainer member 300 is intended to be joined to a distal end 404 of the shaft member 400 by any number of methods including, but not limited to brazing and/or the like. It should be appreciated that the retainer member 300 may be removed from the shaft member 400 at a subsequent later time, e.g., for sterilization purposes. Alternatively, the retainer member 300 and the shaft member 400 may be formed integrally together from a single piece of material.

Figure 22:
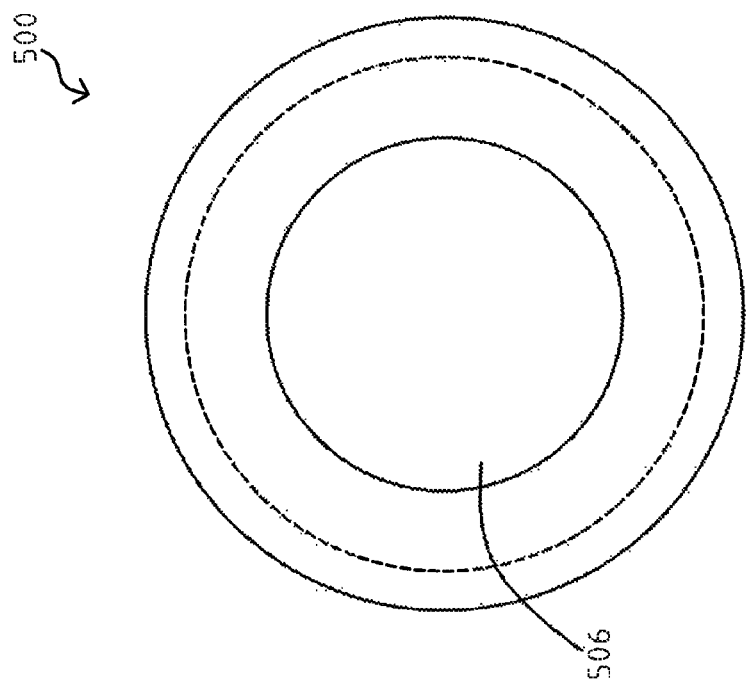
FIG. 22 illustrates a top plan view of a connector member of an optical obturator system, in accordance with a twenty-second embodiment of the present invention.
Figure 21:
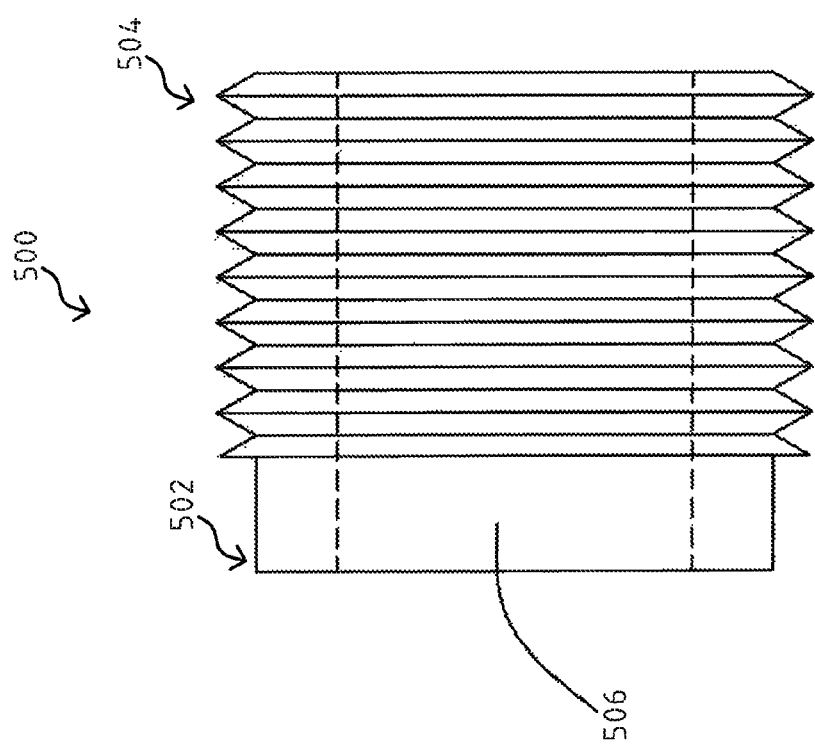
FIG. 21 illustrates an elevational view of a connector member of an optical obturator system, in accordance with a twenty-first embodiment of the present invention.
Figure 23:
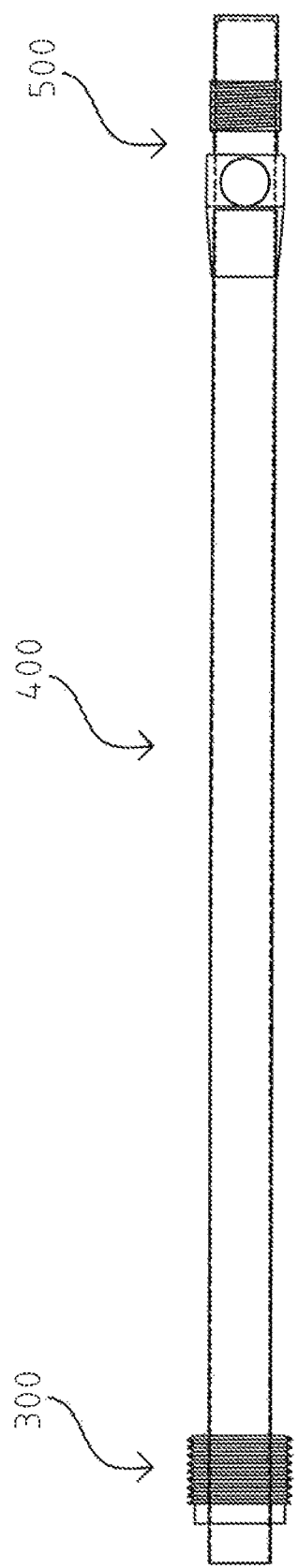
FIG. 23 illustrates an elevational view of a connector member/shaft member/retainer member assembly of an optical obturator system, in accordance with a twenty-third embodiment of the present invention.
Figure 28:
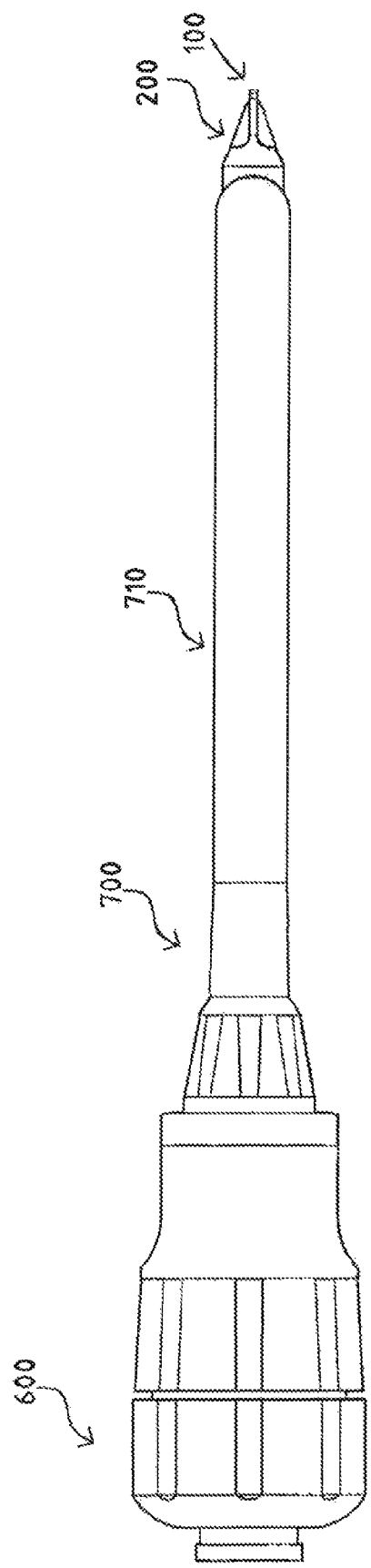
FIG. 28 illustrates an elevational view of an optical obturator/cannula assembly, in accordance with a twenty-eighth embodiment of the present invention.
Figure 29:
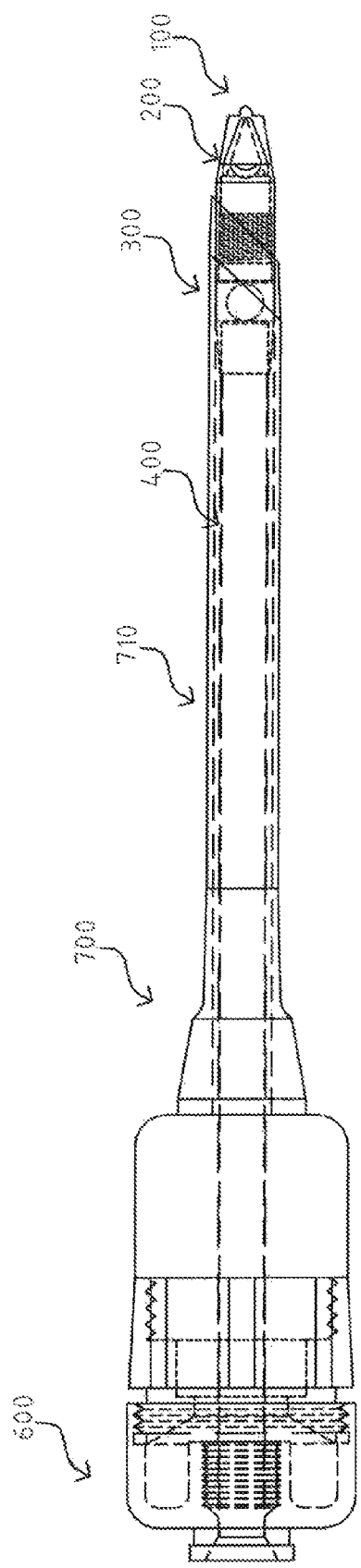
FIG. 29 illustrates a sectional view of an optical obturator/cannula assembly, in accordance with a twenty-ninth embodiment of the present invention.
Figure 30:
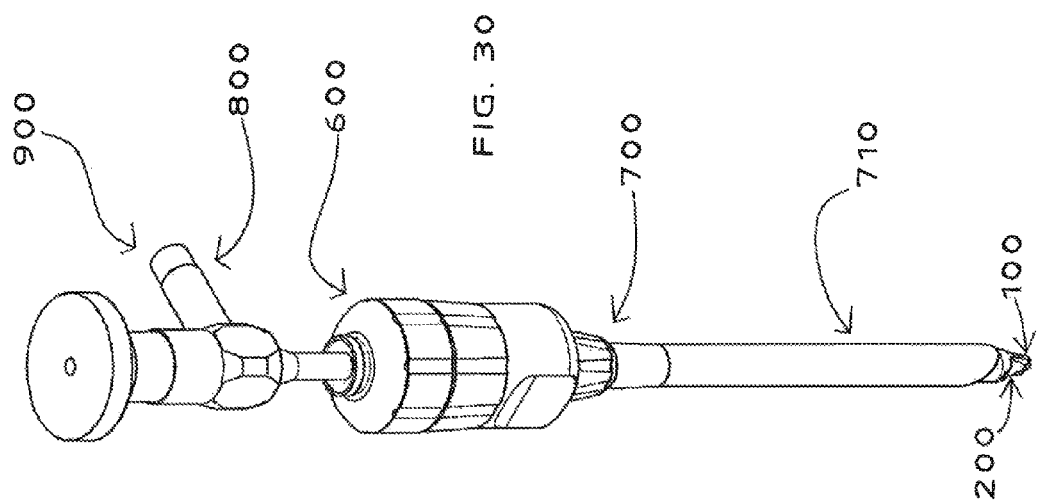
FIG. 30 illustrates an elevational view of an optical obturator/cannula/imaging system assembly, in accordance with a thirtieth embodiment of the present invention.
Figure 31:
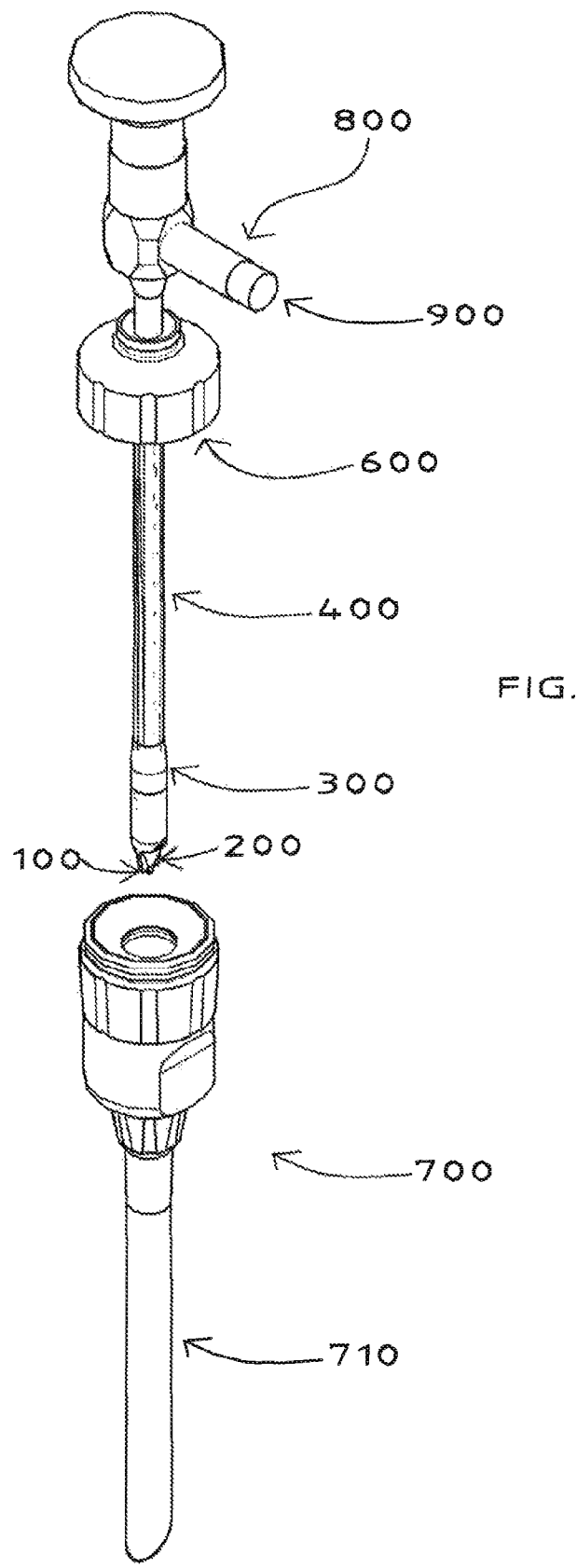
FIG. 31 illustrates a perspective view of an optical obturator/cannula/imaging system assembly, in accordance with a thirty-first embodiment of the present invention.

Referring to the drawings generally, and specifically to FIGS. 21-23, there are shown several views of the connector member 500. The connector member 500 may include a body portion 502 having a threaded surface 504 formed on an external surface thereof. An area defining a bore 506 may be formed through the body portion 502 so as to allow instrumentation to pass there through. By way of a non-limiting example, a proximal portion 406 of the shaft member 400 is intended to be joined to the connector member 500 by placing the distal portion 406 through the bore 506 and securing thereto by any number of methods including, but not limited to brazing and/or the like. It should be appreciated that the shaft member 400 may be removed from the connector member 500 at a subsequent later time, e.g., for sterilization purposes. Alternatively, the connector member 500 and the shaft member 400 may be formed integrally together from a single piece of material.

The connector member 500 may be comprised of a biocompatible material, such as but not limited to stainless steel. The chosen material is preferably suitable to be sterilized by conventional methods numerous times without any appreciable degradation or loss of function.

Referring to the drawings generally, and specifically to FIGS. 24-27, there is shown several views of the handle member 600. The handle member 600 may be comprised of a biocompatible material, such as but not limited to thermoplastics, such as but not limited to polyphenylsulfone, such as but not limited to RADEL® R-5500 (Solvay Advanced Polymers L.L.C., Alpharetta Ga.). The chosen material is preferably suitable to be sterilized by conventional methods numerous times without any appreciable degradation or loss of function.

The handle member 600 may include a body portion 602 having a threaded surface 604 formed on an internal surface thereof. An area defining a bore 606 may be formed through the body portion 602 so as to allow instrumentation to pass there through. One or more seal members (e.g., comprised of silicone) may be provided to prevent and/or reduce possible leakage (e.g., of insufflation gas) as well as to provide a cushioning effect for an imaging device passing therethrough.

By way of a non-limiting example, the connector member 500 may be joined to the handle member 600 by threadingly engaging the threaded surface 604 of the handle member 600 to the threaded surface 504 of the connector member 500. It should be appreciated that the connector member 500 may be removed from the handle member 600 at a subsequent later time, e.g., for sterilization purposes. Alternatively, the handle member 600 and the connector member 500 may be formed integrally together from a single piece of material.

Because the optical obturator system 10 of the present invention may be comprised of materials that can be sterilized many times without any degradation of the materials, the optical obturator system 10, including the major component parts thereof, may be reusable and can thus may be used for a relatively large number of surgical procedures, assuming conventional sterilization techniques are employed after each surgical procedure.

Referring to the drawings generally, and specifically to FIGS. 28-31, there is shown several views of the optical obturator system 10 operably associated with a cannula system 700, including a cannula member 710. An optional port system 800 is shown providing an access system 900 for introducing instrumentation, such as an imaging system, there through so as to be positioned proximate to the transparent window member 200.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An optical obturator system, comprising:
   a tip member having a proximal portion and a distal portion;
   wherein the proximal portion includes a substantially cylindrically shaped body including an area defining an open end and an annular wall member defining a bore extending therefrom towards the distal portion, wherein a threaded portion is formed on a portion of a first wall surface of the bore;
   wherein the distal portion includes a pair of tapered arm members that define a cavity, wherein the cavity communicates with the bore, wherein the arm members are joined together at a terminus of the distal portion to provide a substantially conical surface, wherein a rounded blunt surface is formed on the terminus of the distal portion, wherein one or more cutting surfaces are formed on an edge surface of the arm members, wherein one or more areas defining a curved aperture are formed in a body of the distal portion; and
   a transparent window member having a proximal portion and a distal portion;
   wherein the proximal portion of the transparent window member includes a circular annular surface;
   wherein the distal portion of the transparent window member includes a conical portion, wherein a surface thereof tapers towards a rounded terminus, wherein an area defining a cavity is formed in the proximal portion of the transparent window member and extends into the conical portion proximate to the terminus;
   wherein the transparent window member is configured so as to be operable to be at least partially received within the cavity of the tip member and held in place by the arm members.

2. The optical obturator system according to claim 1, further comprising a retainer member selectively operable to secure the transparent window member in the tip member so as to prevent any relative movement therebetween;
   wherein the retainer member includes a proximal portion and a distal portion;
   wherein the distal portion of the retainer member includes a body member with a threaded surface formed on a portion thereof;
   wherein the retainer member and the tip member are selectively operable to be brought into engagement such that the distal portion of the retainer member is received in the bore of the tip member, such that the threaded surface of the tip member and the threaded surface of the retainer member are brought into threaded engagement with one another.

3. The optical obturator system according to claim 2, wherein a portion of the first wall surface of the tip portion includes an area defining an annular shoulder in proximity to the proximal portion of the threaded portion and further defines a second wall surface of increased diameter as compared to that of the first wall surface.

4. The optical obturator system according to claim 3, wherein the distal portion of the tip portion includes a third wall surface having a decreased diameter as compared to that of either the first wall surface or the second wall surface such that a shoulder is defined between the first wall surface and the third wall surface.

5. The optical obturator system according to claim 4, wherein the proximal portion of the transparent window member has a diameter that is configured so as to allow the transparent window member to pass through the bore of the tip member and past the first, second and third wall surfaces.

6. The optical obturator system according to claim 5, wherein the proximal portion of the retainer member includes an open end and a tapered annular wall surface defining a bore that extends completely through to the distal portion of the retainer member, wherein the annular wall surface includes an area defining an internal annular shoulder surface, wherein at an opposed end of the annular wall surface there is an area defining an external annular shoulder surface.

7. The optical obturator system according to claim 6, wherein at an end of the body member of the retainer member there is formed an annular shoulder surface formed on an internal surface of the bore.

8. An optical obturator system, comprising:
a tip member having a proximal portion and a distal portion;
wherein the proximal portion includes a substantially cylindrically shaped body including an area defining an open end and an annular wall member defining a bore extending therefrom towards the distal portion, wherein a threaded portion is formed on a portion of a first wall surface of the bore;
wherein the distal portion includes a pair of tapered arm members that define a cavity, wherein the cavity communicates with the bore, wherein the arm members are joined together at a terminus of the distal portion to provide a substantially conical surface, wherein a rounded blunt surface is formed on the terminus of the distal portion, wherein one or more cutting surfaces are formed on an edge surface of the arm members, wherein one or more areas defining a curved aperture are formed in a body of the distal portion;
a transparent window member having a proximal portion and a distal portion;
wherein the proximal portion of the transparent window member includes a circular annular surface;
wherein the distal portion of the transparent window member includes a conical portion, wherein a surface thereof tapers towards a rounded terminus, wherein an area defining a cavity is formed in the proximal portion of the transparent window member and extends into the conical portion proximate to the terminus;
wherein the transparent window member is configured so as to be operable to be at least partially received within the cavity of the tip member and held in place by the arm members; and
a retainer member selectively operable to secure the transparent window member in the tip member so as to prevent any relative movement therebetween;
wherein the retainer member includes a proximal portion and a distal portion;
wherein the distal portion of the retainer member includes a body member with a threaded surface formed on a portion thereof;
wherein the retainer member and the tip member are selectively operable to be brought into engagement such that the distal portion of the retainer member is received in the bore of the tip member, such that the threaded surface of the tip member and the threaded surface of the retainer member are brought into threaded engagement with one another.

9. The optical obturator system according to claim 8, wherein a portion of the first wall surface of the tip portion includes an area defining an annular shoulder in proximity to the proximal portion of the threaded portion and further defines a second wall surface of increased diameter as compared to that of the first wall surface.

10. The optical obturator system according to claim 9, wherein the distal portion of the tip portion includes a third wall surface having a decreased diameter as compared to that of either the first wall surface or the second wall surface such that a shoulder is defined between the first wall surface and the third wall surface.

11. The optical obturator system according to claim 10, wherein the proximal portion of the transparent window member has a diameter that is configured so as to allow the transparent window member to pass through the bore of the tip member and past the first, second and third wall surfaces.

12. The optical obturator system according to claim 11, wherein the proximal portion of the retainer member includes an open end and a tapered annular wall surface defining a bore that extends completely through to the distal portion of the retainer member, wherein the annular wall surface includes an area defining an internal annular shoulder surface, wherein at an opposed end of the annular wall surface there is an area defining an external annular shoulder surface.

13. The optical obturator system according to claim 12, wherein at an end of the body member of the retainer member there is formed an annular shoulder surface formed on an internal surface of the bore.

14. An optical obturator system, comprising:
a tip member having a proximal portion and a distal portion;
wherein the proximal portion includes a substantially cylindrically shaped body including an area defining an open end and an annular wall member defining a bore extending therefrom towards the distal portion, wherein a threaded portion is formed on a portion of a first wall surface of the bore, wherein a portion of the first wall surface includes an area defining an annular shoulder in proximity to the proximal portion of the threaded portion and further defines a second wall surface of increased diameter as compared to that of the first wall surface;
wherein the distal portion includes a pair of tapered arm members that define a cavity, wherein the cavity communicates with the bore, wherein the arm members are joined together at a terminus of the distal portion to provide a substantially conical surface, wherein a rounded blunt surface is formed on the terminus of the distal portion, wherein one or more cutting surfaces are formed on an edge surface of the arm members, wherein one or more areas defining a curved aperture are formed in a body of the distal portion, wherein the distal portion includes a third wall surface having a decreased diameter as compared to that of either the first wall surface or the second wall surface such that a shoulder is defined between the first wall surface and the third wall surface;
a transparent window member having a proximal portion and a distal portion;
wherein the proximal portion of the transparent window member includes a circular annular surface;
wherein the distal portion of the transparent window member includes a conical portion, wherein a surface thereof tapers towards a rounded terminus, wherein an area defining a cavity is formed in the proximal portion of the transparent window member and extends into the conical portion proximate to the terminus;

wherein the proximal portion of the transparent window member has a diameter that is configured so as to allow the transparent window member to pass through the bore of the tip member and past the first, second and third wall surfaces;

wherein the transparent window member is configured so as to be operable to be at least partially received within the cavity of the tip member and held in place by the arm members; and a retainer member selectively operable to secure the transparent window member in the tip member so as to prevent any relative movement therebetween;

wherein the retainer member includes a proximal portion and a distal portion;

wherein the proximal portion of the retainer member includes an open end and a tapered annular wall surface defining a bore that extends completely through to the distal portion of the retainer member, wherein the annular wall surface includes an area defining an internal annular shoulder surface, wherein at an opposed end of the annular wall surface there is an area defining an external annular shoulder surface;

wherein the distal portion of the retainer member includes a body member with a threaded surface formed on a portion thereof, wherein at an end of the body member there is formed an annular shoulder surface formed on an internal surface of the bore of the retainer member;

wherein the retainer member and the tip member are selectively operable to be brought into engagement such that the distal portion of the retainer member is received in the bore of the tip member, such that the threaded surface of the tip member and the threaded surface of the retainer member are brought into threaded engagement with one another.

* * * * *

UNITED STATES PATENT AND TRADEMARK OFFICE
CERTIFICATE OF CORRECTION

| | | |
|---|---|---|
| PATENT NO. | : 9,186,173 B2 | Page 1 of 1 |
| APPLICATION NO. | : 13/872856 | |
| DATED | : November 17, 2015 | |
| INVENTOR(S) | : Alan Winfree and Stan Ashburn | |

It is certified that error appears in the above-identified patent and that said Letters Patent is hereby corrected as shown below:

On the Title page, at item (73), the Assignee is misidentified in that the words "Specialty Care" should be replaced with the term --SpecialtyCare--.

Signed and Sealed this
Twenty-second Day of March, 2016

Michelle K. Lee
*Director of the United States Patent and Trademark Office*